(12) United States Patent
Bianchetti et al.

(10) Patent No.: US 6,793,490 B2
(45) Date of Patent: Sep. 21, 2004

(54) DENTAL HANDPIECE FOR THE POLYMERIZATION OF PHOTOSETTING COMPOUNDS OR RESINS, COMPATIBLE WITH THE POWER SUPPLY OF OTHER HANDPIECES

(75) Inventors: Fernando Bianchetti, Chiavari (IT); Domenico Vercellotti, Sestri Levante (IT)

(73) Assignee: Mectron S.r.l., Genoa (IT)

( * ) Notice: Subject to any disclaimer, the term of this patent is extended or adjusted under 35 U.S.C. 154(b) by 244 days.

(21) Appl. No.: 10/155,762

(22) Filed: May 24, 2002

(65) Prior Publication Data

US 2003/0219694 A1 Nov. 27, 2003

(51) Int. Cl.$^7$ ............................. A61C 19/00; A61C 1/18
(52) U.S. Cl. ..................... 433/29; 433/114; 433/119
(58) Field of Search .................... 433/29, 114, 118, 433/119, 126

(56) References Cited

U.S. PATENT DOCUMENTS

| | | | |
|---|---|---|---|
| 4,080,737 A | 3/1978 | Fleer | |
| 4,514,172 A * | 4/1985 | Behringer | 433/126 |
| 4,725,232 A | 2/1988 | Hatakeyama | 433/98 |
| 5,634,711 A | 6/1997 | Kennedy et al. | 362/119 |
| 6,095,810 A * | 8/2000 | Bianchetti | 433/29 |
| 6,331,111 B1 * | 12/2001 | Cao | 433/29 |

FOREIGN PATENT DOCUMENTS

| | | | |
|---|---|---|---|
| EP | 1 090 607 A1 | * | 4/2001 |
| EP | 1 090 608 A1 | * | 4/2001 |
| EP | 1 103 232 A1 | * | 5/2001 |

* cited by examiner

*Primary Examiner*—Ralph A. Lewis
(74) *Attorney, Agent, or Firm*—Sheridan Ross PC

(57) ABSTRACT

A dental handpiece for the polymerization of photosetting resins or compounds comprising as its polymerizing light source, at least one LED incorporated in the handpiece, the electrical supply signal for the LED light source being drawn from connectors of other types of hand pieces and being processed by means of an appropriate electronic circuit in order to make the electrical supply signal suitable for bias of said LED light source.

11 Claims, 3 Drawing Sheets

DENTAL HANDPIECE FOR THE POLYMERIZATION OF PHOTOSETTING COMPOUNDS OR RESINS, COMPATIBLE WITH THE POWER SUPPLY OF OTHER HANDPIECES

BACKGROUND OF THE INVENTION

The present invention relates to a dental handpiece for the polymerization of photosetting compounds or resins compatible with the power supply of other handpieces.

The invention refers in particular to an instrument employed by dental surgeons for the polymerization of photosetting compounds or resins utilised especially in dental prostheses, Photosetting resins are applied in a semifluid state to patients' dental prostheses and are then hardened by a polymerization process. Such a polymerization process involves heating the resins for a certain length of time, using a light source that emits blue light, i.e. having an emission spectrum with a wavelength centered around 470 nm.

Handpieces according to the prior art currently use halogen lamps as their light source. The light coming from the halogen lamps is filtered by dichroic filters, so that a blue light having a light spectrum with a wavelength between 430 and 510 nm is obtained. The light emerging from the dichroic filters is transported, through optic fibres, to the outlet of the dental handpiece, enabling the dentist to direct it onto the resin to be polymerized, applied to the patient's dental prosthesis.

The known dental handpieces using halogen lamps as polymerizing lamps have various drawbacks.

In order to achieve polymerization of the resin, the light emerging from the dental handpiece must have a power of approximately 500 mW. Since halogen lamps have a very low power efficiency (efficiency value $\eta=0.5-1\%$), this results in a high energy dissipation by the polymizering lamps, which reaches values between 50 and 100 W.

For this reason, handpieces for the polymerization of photosetting compounds must have a special power supply, able to supply the polymerizing lamps with a power that ranges from 50 to 100 W. Consequently, the seats in which the patients sit, normally known as dental chair units, provide a connector element connected to the power supply and specifically designed for the polymerizing handpiece.

Furthermore, with the output power that can be obtained from halogen lamps, rather long resin polymerization times are required; this can be very tiresome both for the patient undergoing the procedure and for the dental surgeon who has to perform it.

In an attempt to reduce resin polymerization times, handpieces with different light sources have been put on the market. Handpieces are per se known that use as their light source gas-discharge lamps (plasma torches) that emit high-power white light, which is filtered in order to obtain a light beam with an emission spectrum centred on blue. Also known are dental handpieces using laser as their light source, which directly transmit a light beam with an emission spectrum centred on blue.

With this type of dental handpiece it is possible to obtain a light beam with a power output approximately ten times greater compared to that obtained with halogen lamps, therefore shorter polymerization times are achieved. However, such dental handpieces, apart from being very expensive, have the problem of needing to dissipate a large amount of heat and inevitably they must provide a heat dissipation or cooling system, making them excessively bulky and heavy. Furthermore, such heat dissipation systems often include fans driven by motors which must be powered by the dedicated electrical supply of the polymerizing handpiece.

Also known, especially at an experimental level, are handpieces for polymerization of photosetting compounds using as their light source LEDs that emit in the blue range.

All known handpieces using halogen lamps, plasma torches, laser or LEDs as their light source, have an independent electrical supply system, dedicated soleley to the electrical supply of said light sources. This makes the dental handpiece bulky and lacking in versatility because of the purpose-built circuitry provided for such light sources and also the need to provide the dental chair unit with special connectors for the power supply of such handpieces.

BRIEF DESCRIPTION OF THE INVENTION

The object of the invention is to eliminate said drawbacks, providing a dental handpiece for polymerization of photosetting compounds or resins that is compatible with the power supply of other handpieces.

A further object of the present invention is to provide a handpiece of reduced dimensions and bulk that is versatile, economical and easy to produce.

The handpiece according to the invention comprises a connector element shaped so as to be able to connect to external electrical connectors utilised for other types of handpieces, such as for example the handpiece or ultrasound scaler for removal of plaque and caries, or the dental turbine for cleaning and washing dental prostheses.

This is made possible thanks to the fact that in the handpiece according to the invention LEDs that emit in the blue range are used as the light source. In fact LEDs require a decidedly lower power supply than halogen lamps, plasma torches or laser. This has made it possible to take the electrical supply for bias of the LEDs directly from the electrical supply circuit provided in the external connector of other types of handpieces.

In the case of connection of the handpiece for polymerization according to the invention to the connector of an ultrasound scaler, the electrical energy for bias of the LEDs is taken from the electrical circuit provided in the connector of the scaler and destined to supply the ultrasound transducer of the scaler.

For this purpose, in the handpiece according to the invention, an equivalent resonator circuit is provided that must tune the resonance frequency of the supply circuit provided in the external connector of the scaler. Downstream of the equivalent resonance circuit and upstream of the LED assembly of the polymerizing handpiece, a voltage and current stabilizer or regulator is provided in order to generate a constant voltage and direct current signal for correct bias of the LEDs.

Dental turbines include a light source to illuminate the work surface. For the electrical supply to this light source of the dental turbine, the external connectors of dental turbines carry an electrical supply signal taken from an electrical supply source. In the case of connection of the handpiece according to the invention to an external connector for dental turbines, the supply of the LEDs for polymerization is taken from the electrical supply carried by the external connector of the turbine.

In this case the voltage supplied by the external connector is too low to be able to supply the LEDs, therefore an electronic voltage booster or step-up transformer circuit capable of providing an adequate voltage to bias the LEDs is provided inside the handpiece according to the invention. Downstream of the step-up transformer circuit a voltage and current stabilizing circuit is provided to maintain a constant voltage and direct current during power supply of the LEDs.

The advantages of the handpiece for the polymerization of photosetting compounds according to the invention appear evident. Since it can adapt to the connectors used for the power supply of handpieces of other types, it allows the connectors and circuitry specifically dedicated to its supply to be eliminated from the dental chair unit, with considerable economic advantages as regards size and complexity.

BRIEF DESCRIPTION OF THE DRAWING

Further characteristics of the invention will be made clearer by the detailed description that follows, referring to purely exemplary and therefore non-limiting embodiments thereof, illustrated in the appended drawing, in which.

DETAILED DESCRIIPTION OF THE INVENTION

Figure 1:
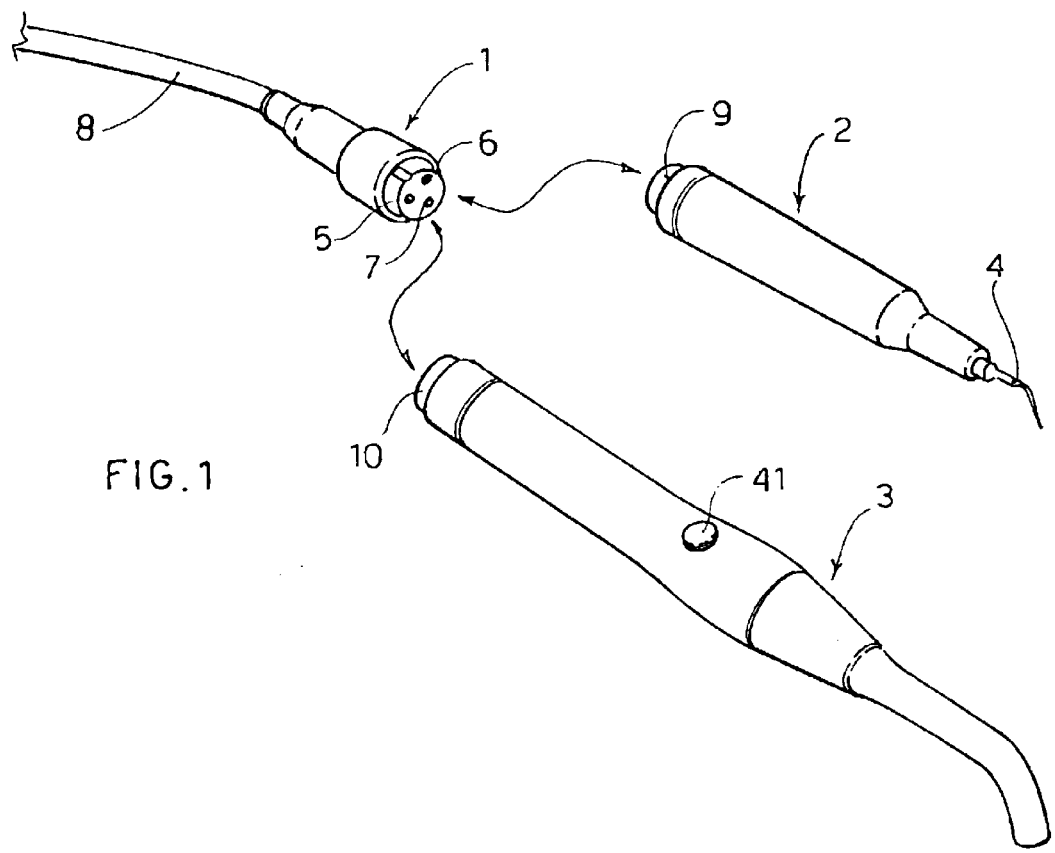
FIG. 1 is a perspective view of a first embodiment of the invention illustrating the handpiece for the polymerization of thermosetting compounds according to the invention in a configuration compatible with an ultrasound scaler.

FIG. 1 shows an external connector element 1, a handpiece or ultrasound scaler 2 for removal of tartar and scale and a dental handpiece 3 for polymerization of photosetting compounds or resins, according to a first embodiment of the invention.

The scaler 2, per se known, comprises a hollow cylindrical body inside which is positioned a piezoceramic resonator, which acts as a sound wave concentrator to set in vibration a hook-shaped workpiece suitable for removal of plaque and scale from the patient's teeth.

In order to act as a vibrator, the piezoceramic resonator of the scaler 2 must be supplied with an alternating sinusoidal voltage of about 160–200 Volt r.m.s. at an oscillation frequency ranging from 26 KHz to 30 KHz. This supply signal is provided by the connector 1, per se known.

The external connector 1, specially designed for the scaler 2, is provided with two holes 5 and 6 for electrical coupling and a hole 7 for hydraulic coupling. The holes 5 and 6 are connected to respective electrical supply wires upstream of which an electrical transformer (not shown) is provided. Said transformer, generally provided on a dental chair unit, serves to transform the mains voltage (220 Volt alternating current) into a sinusoidal voltage of 160–200 Volt r.m.s. at a frequency of 26–30 KHz, which is suitable for operating the piezoceramic resonator of the scaler 2. The hole 7, on the other hand, is connected to a hydraulic system to send jets of water under pressure which are conveyed through the scaler 2 to exit from the tip of the workpiece 4. The electrical supply wires and the hydraulic supply tube are enclosed in a sheath 8 and directed toward the electrical supply source and the hydraulic supply source provided in the dental chair unit or in the electrical and hydraulic network.

The scaler 4, in order to be able to couple to the connector element 1, must have a complementary connecting element 9 that provides two electrical contacts that engage inside the holes 5 and 6 and a hydraulic coupling element that engages in the hole 7.

The dental handpiece 3 for the polymerization of photosetting compounds or resins uses LEDs 30 as the light source. In the present embodiments of the invention a group of semiconductor LEDs 30 integrated on a printed circuit board 31 is shown (FIG. 2), although other types of LED commonly available on the market can be employed.

Consequently the handpiece 3 for the polymerization of photosetting compounds according to the invention, in order to be able to connect to the connector 1 of the scaler 2, has a connector element 10 substantially similar to the connector element 9 of the scaler 2.

Figure 2:
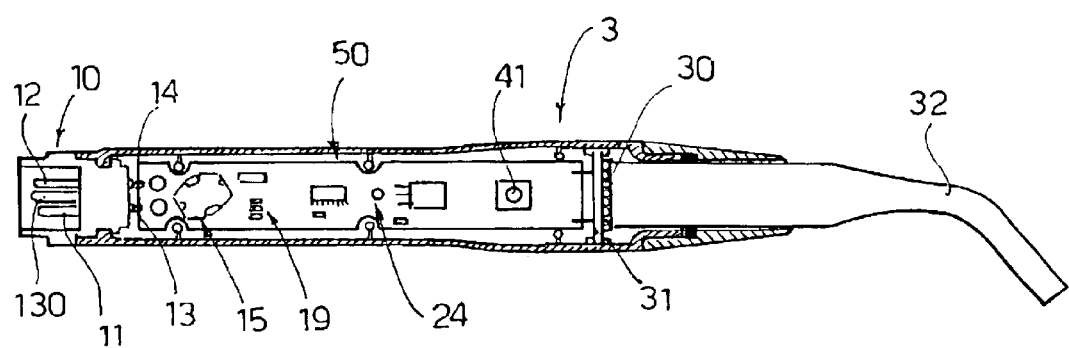
FIG. 2 is an axial sectional view of the handpiece for polymerization of photosetting compounds of FIG. 1.

As shown in FIG. 2, the connector element 10 provides two electrical contacts 11 and 12 that engage respectively in the holes 5 and 6 of the electrical circuit of the connector 1 and a coupling element 130 that engages in the hole 7 of the hydraulic circuit of the connector 1. The coupling element 130 serves simply to plug the hole 7, because in the polymerizing handpiece 3 there is no need to have jets of water at high pressure.

The electrical contacts 11 and 12 are connected to respective electrical wires 13 and 14 in turn connected to an electronic circuit 50 that serves to supply the LEDs 30. The electronic circuit 50 has a resonant circuit 15. The resonant circuit 15 can be any type of resonant circuit able to tune the frequency of 26–30 KHz of the electrical supply signal coming from the external connector element 1.

Figure 3:
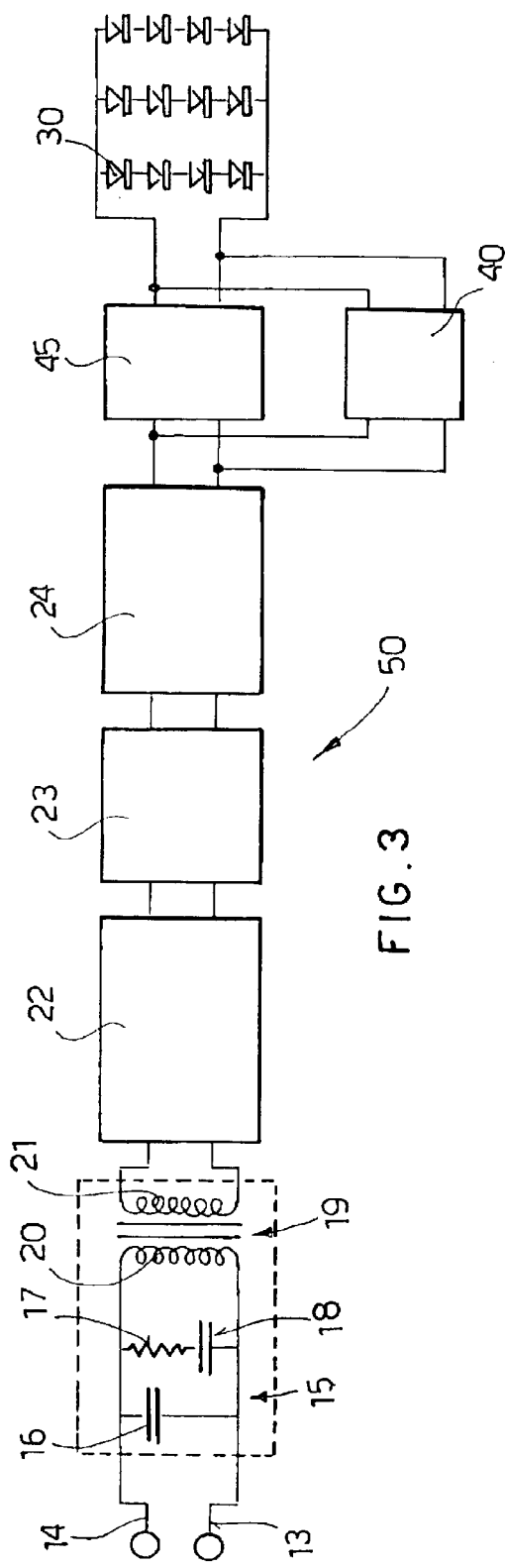
FIG. 3 is an electrical block diagram illustrating the electronic circuit for supply of the handpiece of FIG. 2.

In FIG. 3, by way of example, the resonance circuit 15 is made up of a parallel resonator comprising a capacitance 16 in parallel to a resistance 17 in series with a capacitance 18.

Downstream of the resonating circuit 15 a transformer 19 is provided to transform the output voltage from the resonating circuit 15 into a voltage suitable for bias of the LEDs 30. The voltage transformer 19 can be made in various ways. FIG. 3 shows a primary winding 20 mutually coupled with a secondary winding 21.

Downstream of the transformer 19 a rectifier 22 can be provided to rectify the wave shape of the electrical supply signal. Downstream of the rectifier 22 a filter 23 can also be provided to filter possible disturbances of the electrical supply signal.

The supply signal from the filter 23 is sent to a voltage and current stabilizer 24 able to generate as its output a constant voltage signal and a direct current signal for bias of the LEDs 30.

Depending on the type of LEDs used, they may require different bias currents and voltages. By way of example, in the present embodiment semiconducter LEDs 30, preferably gallium arsenide, are used, integrated in a printed circuit board 31 disposed inside the body of the handpiece 3. The LEDs 30 are coupled to an optical fibre or light guide 32 to convey the light to the head of the handpiece, so as to be able to direct it toward the point of work.

Each gallium arsenide LED 30 requires a bias voltage of about 3.3 V and a bias current of about 20 mA direct or greater currents for pulse supply. In the present embodiment, FIG. 3 shows a matrix of twelve LEDs 30 made by means of three parallel arrays, each array comprising four LEDs in series. In this case the voltage from the voltage and current stabilizer 24 will be greater than or equal to 13.2 V, in order to have a voltage drop of 3.3V on each LED 30.

Clearly other configurations of the LEDs 30 are possible. The LEDs 30 can be connected in series or in parallel depending on the voltage and current from the voltage and current stabilizer 24.

Upstream and downstream of the voltage stabilizer 24 a switch 45 is provided, shown downstream in FIG. 3. When the switch 45 is turned on or off the supply to the LEDs 30 is enabled or disabled. The switch 45 is controlled by a pushbutton 41 protruding outward from the body of the handpiece 3, so that it can be pushed by an operator. The switch 45 can be connected to a timer or system clock 40.

In this manner when the operator presses the button 41, the switch 45 enables the supply of the LEDs 30 that begin to emit blue light. At the same time the system clock 40 begins to count for a fixed period of time, necessary for polymerisation of photosetting compounds (for example, 20 seconds). After this period of time the power supply of the LEDs 30 is turned off and therefore LEDs turn off. Pressing the button 41 during the operating cycle causes the turning off of the LEDs and resets the system clock 40 for the next cycle.

Figure 6:
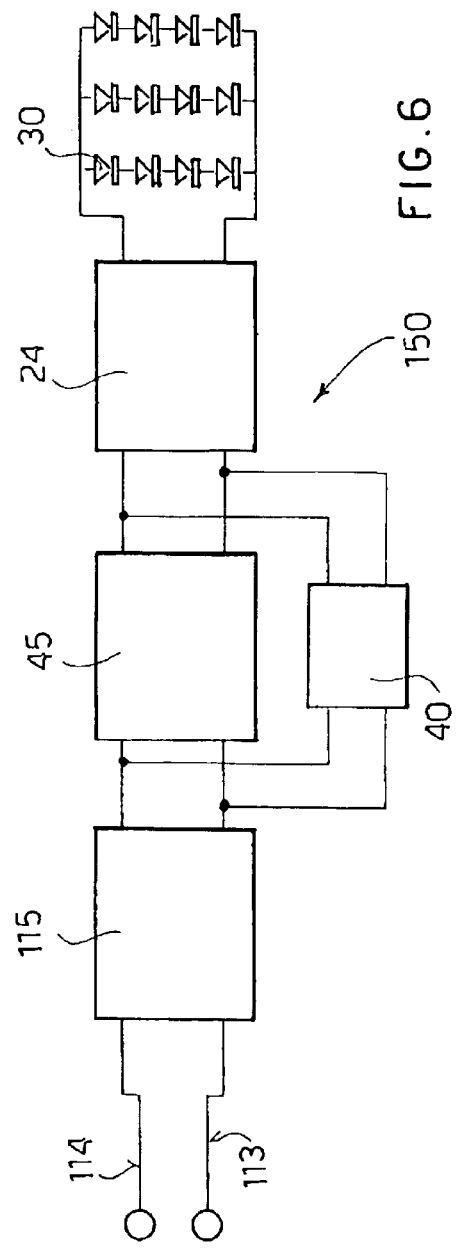
FIG. 6 is an electrical block diagram, illustrating the electronic circuit for the supply of the handpiece of FIG. 5.
Figure 4:
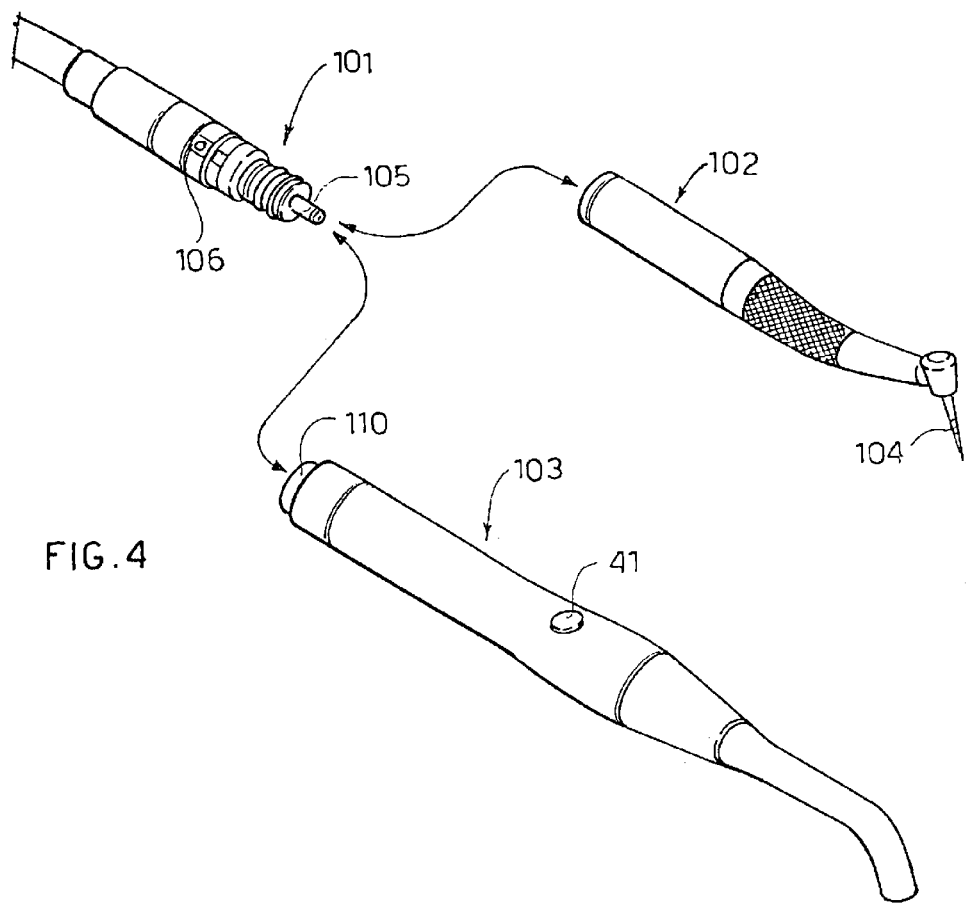
FIG. 4 is a perspective view of a second embodiment of the invention, illustrating the handpiece for polymerization of photosetting compounds according to the invention in a configuration compatible with a dental turbine.
Figure 5:
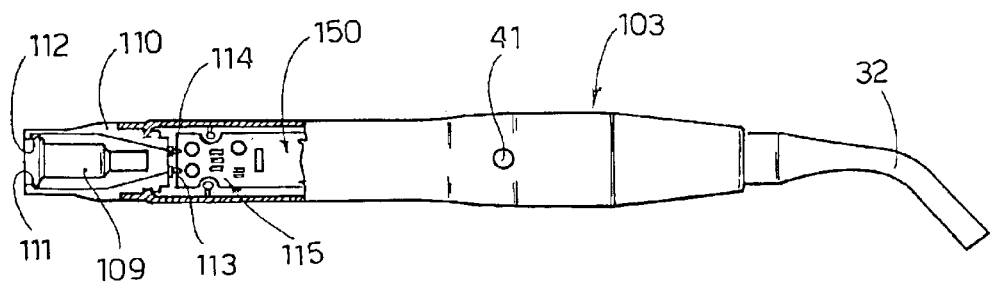
FIG. 5 is an axial sectional view of the handpiece for polymerization of photosetting compounds of FIG. 4.

In FIGS. 4–6 a second embodiment of the invention is shown in which similar or corresponding elements are denoted by the same reference numerals used in the first embodiment.

FIG. 4 shows an external connector element 101, a dental turbine handpiece 102 for dental cleaning and a dental handpiece 103 for the polymerization of photosetting resins or compounds according to a second embodiment of the invention.

The turbine 102 has a hollow cylindrical body that ends in a pin element 104 that is set in rotation by means of a hydraulic or pneumatic system. The pin element 104 also has an air and water passage through which air and/or water is sprayed toward the patient's teeth. The turbines 102 also have a light source, normally a lamp, which conveys the light toward the work surface through an optical fibre.

The connector 101 must therefore have a hydraulic and penumatic supply for the turbine 102 and an electrical supply for the light source of the turbine 102. The connector 101 can be of various types and models. There are essentially two categories available on the market: fast connectors and locking nut connectors.

FIG. 4 shows a fast connector 101 that has a hollow central tang 105 in which the water passage, the air passage and a possible air return passage are provided.

Two electrical contacts 106 (only one visible in FIG. 4), disposed diametrically opposite each other, are provided on the outer circumference of the connector 101. Said electrical contacts can the electrical supply for the lamp of the turbine 102. For this purpose the supply voltage is very low. In fact a voltage of about 2.75V is sufficient to light the lamp of the turbine 102.

The handpiece 103 for the polymerization of photosetting compounds is substantially similar to the handpiece 3 of the first embodiment. The handpiece 103 also has as its light source a plurality of LEDs 30 integrated in a printed circuit board 31.

The handpiece 103 has a connector element 110 shaped so as to be able to be applied to the connector 101 of the turbine 102. As shown in FIG. 5, the outer connector 110 has two electrical contacts 111 and 112 destined to go into contact with the respective contacts 106 provided on the connector 101. The connector 110 has a housing 109 able to accommodate the tang 105 of the connector 101. The housing 109 is a disabled water and air circuit, since there is no need for water and air under pressure in the handpiece 103.

The electrical contacts 111 and 112 are connected to the respective electrical wires 113 which carry the electrical supply to an electronic supply circuit 150. The electronic supply circuit 150 has a voltage booster or step-up transformer 115. The voltage carried by the electrical wires 113 and 114 is the voltage taken from the external connector 101. Thus the voltage at the input to the step-up transformer 115 is about 2.75 V which is too low for polarization of the LEDs 30. Consequently the step-up transformer 115 raises the voltage so as to have an adequate bias voltage for the LEDs 30 at its output. The step-up transformer 115 can be, for example, a PWM (Pulse Width Modulation) generator which is able to increase the voltage.

Downstream of the step-up transformer 115 a timer 40 is provided which, as in the first embodiment, is connected to a switch, in turn connected to a pushbutton 41 that can be pressed by the operator for turning on or turning off of the LEDs 30.

The voltage and current from the step-up transformer 115 are sent through a voltage and current stabiliser 24, substantially similar to that used in the first embodiment, so that at the output from the voltage and current stabilizer 24 there is a constant voltage and a direct current for bias of the LEDs 30.

Various modifications and changes within the reach of a person skilled in the art can be made to the present embodiments without thereby departing from the scope of the invention expressed in the appended claims.

What is claimed is:

1. A dental handpiece for the polymerization of photosetting compounds or resins using as its polymerizing light source at least one LED, comprising:

a connector element that can be adapted to external connectors of other types of handpieces carrying an electrical supply in order to take said electrical supply, and an electronic circuit connected to said connector element to process the electrical supply signal to supply said polymerizing light source wherein said connector element can be adapted to an external connector of a handpiece or ultrasound scaler in order to take electrical power destined for the resonator of the scaler and convey it, through the electronic circuit, toward the polymerizing light source and, wherein said electronic circuit provides a resonance circuit able to tune a supply frequency coming from said connector element, said frequency being set to vibrate the resonator provided in the scaler.

2. The dental handpiece of claim 1, wherein said resonance circuit is a parallel resonator that provides a capacitance in parallel to a resistance in series with a capacitance.

3. The dental handpiece of claim 1, wherein a voltage transformer is provided downstream of the resonance circuit to generate an adequate bias voltage for said polymerizing light source.

4. The dental handpiece of claim 1, wherein said electronic supply circuit provides a rectifier to rectify the electrical supply signal for bias of the polymerizing light source.

5. The dental handpiece of claim 1, wherein said electronic supply circuit provides a filter to filter the disturbances of the electrical supply system.

6. The dental handpiece of claim 1, wherein said connector element of the handpiece for polymerization of photosetting compounds can be adapted to the external connector of a dental turbine in order to take the electrical power destined to the light source of the dental turbine and convey it through the electornic circuit towards the polymerizing light source of the handpiece.

7. The dental handpiece of claim 1, wherein said electornic supply circuit provides a step-up transformer to generate an adequate bias voltage for the polymerizing light source.

8. The dental handpiece of claim 7, wherein said step-up transformer is a PWM (Pulse width Modulation) booster able to increase the output voltage and current to have an adequate bias voltage and current for the polymerizing light source.

9. The dental handpiece of claim 1, wherein a voltage and current stabilizer is provided in said supply circuit of said handpiece upstream of the at least one LED to supply said at least one LIED with a constant voltage signal and a direct current signal for bias thereof.

10. The dental handpiece of claim 1, wherein a switch is provided in said supply circuit of said handpiece, said switch controlled by a pushbutton that can be pressed by the operator to turn said polymerizing light source on and off.

11. The dental handpiece of claim 10, wherein said switch is connected to a timer that closes the switch for a period of time necessary for polymerization of the photosetting compounds so as to direct the light emitted by the polymerizing light source onto the photosetting compounds for said necessary period of time.

* * * * *